United States Patent [19]

Nonn

[11] Patent Number: 5,087,768
[45] Date of Patent: Feb. 11, 1992

[54] PROCESS FOR THE PURIFICATION OF DIHYDROXYBIPHENYLS

[75] Inventor: Alain Nonn, Pfastatt, France

[73] Assignee: Rhone-Poulenc Chimie, Courbevoie Cedex, France

[21] Appl. No.: 593,268

[22] Filed: Oct. 1, 1990

Related U.S. Application Data

[63] Continuation of Ser. No. 372,251, Jun. 27, 1989, abandoned.

[30] Foreign Application Priority Data

Jun. 29, 1988 [FR] France ............... 88 08725

[51] Int. Cl.$^5$ ............... C07C 37/68; C07C 37/84
[52] U.S. Cl. ................... 568/730; 568/724; 568/748
[58] Field of Search ............ 568/724, 722, 723, 730, 568/747, 748; 560/141

[56] References Cited

U.S. PATENT DOCUMENTS

| | | | |
|---|---|---|---|
| 2,278,634 | 4/1942 | Barnes | 560/141 |
| 2,829,175 | 4/1958 | Bowman et al. | 568/724 |
| 3,383,395 | 5/1968 | Schmulke | 560/141 |
| 4,170,711 | 10/1979 | Orlando et al. | 560/141 |
| 4,885,407 | 12/1989 | Fox et al. | 568/724 |

FOREIGN PATENT DOCUMENTS

| | | | |
|---|---|---|---|
| 1155452 | 10/1963 | Fed. Rep. of Germany | 568/724 |
| 19159 | 9/1964 | Japan | 568/724 |
| 16536 | 7/1965 | Japan | 568/724 |
| 197708 | 9/1977 | U.S.S.R. | 568/724 |

*Primary Examiner*—Werren B. Lone
*Attorney, Agent, or Firm*—Finnegan, Henderson, Farabow, Garrett and Dunner

[57] ABSTRACT

A process for the purification of dihydroxybiphenyls, preferably 4,4'-dihydroxybiphenyl, by acylation of the preparation medium of the dihydroxybiphenyl and selective precipitation of the biphenyl diester (diacetylbiphenyl), followed by conversion of the biphenyl diester to dihydroxybiphenyl.

6 Claims, No Drawings

PROCESS FOR THE PURIFICATION OF DIHYDROXYBIPHENYLS

This is a continuation of application Ser. No. 07/372,251, filed June 27, 1989, abandoned.

The present invention relates to a process for the purification of a dihydroxybiphenyl. It relates more particularly to the purification of 4,4'-dihydroxybiphenyl.

4,4'-Dihydroxybiphenyl is prepared, for example, according to U.S. Pat. No. 4,475,000 by hydrolysis of 4,4'-dibromobiphenyl in the presence of a copper catalyst at a temperature greater than 300° C. During the preparation of the 4,4'-dibromo derivative, it is impossible to eliminate the presence of monobromo derivatives or of derivatives dibrominated in positions other than the 4,4'-position.

During the hydrolysis of this complex mixture, or even of the pure dibromo derivative, formation of monohydroxybiphenyl and small quantities of heavier polycondensation products containing at least two biphenyl residues always takes place. Because these different compounds have very closely related structures and physical properties which are very similar, they are difficult to separate.

4,4'-Dihydroxybiphenyl can also be prepared according to U.S. Pat. No. 4,447,656 by oxidative coupling of di-tert-butylphenol followed by reduction and dealkylation. Other isomers, such as 2,2',6,6'-tetra-tert-butyl-p,p'-biphenol, are formed in the course of this reaction.

In the course of these successive reactions, as in the patent previously cited, incomplete reactions form monohydroxybiphenyls and secondary reactions form heavy polycondensate derivatives such as, for example, tetrahydroxytetraphenyls or bis(hydroxybiphenyl) ethers.

4,4'-Dihydroxybiphenyl is a starting material used in the synthesis of polymers of high technical grade where it is necessary to have polymeric chains free from branching. It is thus important that the 4,4'-dihydroxybiphenyl be as pure as possible.

The present invention enables an essentially pure solution of dihydroxybiphenyl to be obtained starting from solutions containing dihydroxybiphenyl resulting from the hydrolysis of dibromobiphenyls or from the dealkylation of tetra-tert-butylbiphenols.

The subject of the present invention is a process for the purification of 4,4'-dihydroxybiphenyl, wherein an esterification of the reaction mixture resulting from the preparation of the biphenyl is carried out with a derivative of acetic acid in the presence of an acid, and the biphenyl diester is allowed to crystallize. Following crystallization, the biphenyl diester can be converted by means known to those skilled in the art to essentially pure 4,4'-dihydroxybiphenyl. For example, the dihydroxybiphenyl can be saponified with an alkali, such as NaOH or KOH, to obtain the 4,4'-dihydroxybiphenyl.

This particularly simple and economic process enables a biphenyl having a purity of the order of 99% to be obtained starting from solutions containing about 15% by weight of secondary products.

An acid derivative, as defined herein, includes the acid halides, preferably the acid chloride, as well as the acid anhydrides or the esters. Of all of these acid derivatives, acetyl chloride or acetic anhydride is preferred.

The esterification can be carried out in the presence of an esterification catalyst, which may be an organic acid, such as, in particular:
benzenesulfonic acid
methanesulfonic acid
trifluoroacetic acid
trifluoromethanesulfonic acid;
an inorganic acid, such as, in particular;
sulfuric acid
hydrochloric acid; and
an acid resin, such as, in particular: a benzenesulfonic resin.

The esterification can take place in the presence or the absence of a solvent.

When a solvent is used, the solvent can be an acid formed during the esterification. Other representative solvents include the halogenoalkanes, such as dichloroethane; the aromatic solvents, such as, in particular, toluene; the esters, such as ethyl acetate; the ketones, such as methyl isobutyl ketone; and the alcohols, such as methanol.

The solvents cited above are illustrative only. The esterification is preferably carried out in acetic acid.

With regard to the reaction conditions, the esterification is preferably carried out at a temperature greater than or equal to 80° C. and more preferably at the reflux temperature of the reaction medium.

The esterification reaction is preferably carried out under a pressure greater than or equal to atmospheric pressure.

The crystallization of the biphenyldiester can be routinely carried out by any technique known to those skilled in the art. For example, the reaction medium can be cooled or evaporated under atmospheric pressure or under reduced pressure.

The invention will be described more completely with the aid of the following examples, which must not be regarded as limiting the invention.

EXAMPLE 1

Starting from a mixture containing:
87% of 4,4'-dihydroxybiphenyl
2% of 4-hydroxybiphenyl and
11% of compounds of the formulae

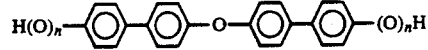

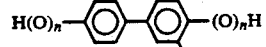

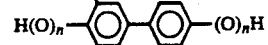

in which n is 0 or 1, 32.75 g of the above mixture were esterified in the following way:
suspension in 150 ml of acetic acid;
addition of 36.5 g of acetic anhydride and of 0.28 g of para-toluenesulfonic acid;
refluxing for three hours with magnetic stirring;
slow cooling with magnetic stirring: white crystals form;
after filtration, the crystals were washed with water, then dried in vacuo at 50° C.

The yield was 90%.

Determination by high performance liquid chromatography gave a purity greater than 99.5%.

Melting point: 160° C.

| Microanalysis: | theoretical | found |
|---|---|---|
| C: | 71.10 | 71.15 |
| H: | 5.22 | 5.17 |

EXAMPLE 2

Starting from a mixture containing:
84.9% of 4,4'-dihydroxybiphenyl and
15.1% of 2,2'-dihydroxybiphenyl,
5.58 g of the above mixture were esterified according to the same method as for Example 1.

The yield of 4,4'-diacetoxybiphenyl was 90%. The purity was greater than 99.5%

Melting point: 160° C.

EXAMPLE 3

10.7 g of the mixture used in Example 1 were esterified under the following conditions:
dilution in 60 ml of methyl isobutyl ketone;
addition of 14.0 g of acetic anhydride and of 0.11 g of para-toluenesulfonic acid;
heating at 100° C. for 3 hours;
cooling;
filtering-off of the crystals.
The yield of crystals: 79%.
Purity: 98%
0.1% of 4-acetoxybiphenyl
0.1 of 4-acetoxy-4'-hydroxybiphenyl

I claim:

1. A process for the purification of a dihydroxybiphenyl, comprising the steps of:
   (1) esterifying, with a derivative of an acetic acid in the presence of a strong acid, a reaction product mixture containing a dihydroxybiphenyl and at least one other by-product resulting from a reaction used to prepare said dihydroxybiphenyl, to form a biphenyl diester, said reaction is selected from the hydrolysis of dibromobiphenyls or the dealkylation of tetra-tert-butylbiphenols;
   (2) allowing the biphenyl diester prepared in step (1) to crystallize;
   (3) recovering said crystallized biphenyl diester; and
   (4) converting said biphenyl diester to a dihydroxybiphenyl.

2. The process of claim 1, wherein said dihydroxybiphenyl is 4,4'-dihydroxybiphenyl.

3. The process of claim 2, wherein said derivative of acetic acid is acetic anhydride.

4. The process of claim 2, wherein the strong acid is selected from the group consisting of sulfuric acid, hydrochloric acid, benzenesulfonic acid, para-toluenesulfonic acid, trifluoromethanesulfonic acid and a benzenesulfonic resin.

5. The process of claim 4, wherein the strong acid is para-toluenesulfonic acid.

6. The process of claim 1, wherein the reaction mixture to be esterified in step (1) includes a solvent.